United States Patent [19]
Assenheimer Downs

[11] Patent Number: 5,782,794
[45] Date of Patent: Jul. 21, 1998

[54] INFRARED TREATED TAMPON APPLICATORS

[75] Inventor: Suzanne E. Assenheimer Downs, Ho-Ho-Kus, N.J.

[73] Assignee: Playtex Products, Inc., Westport, Conn.

[21] Appl. No.: 788,472

[22] Filed: Jan. 28, 1997

[51] Int. Cl.⁶ .................................. A61F 13/20
[52] U.S. Cl. ........................................ 604/15
[58] Field of Search ........................... 604/11–18

[56] References Cited

U.S. PATENT DOCUMENTS

| | | |
|---|---|---|
| 2,518,486 | 8/1950 | Mende. |
| 3,724,462 | 4/1973 | Hanke. |
| 3,882,196 | 5/1975 | Hanke. |
| 3,882,869 | 5/1975 | Hanke. |
| 3,911,917 | 10/1975 | Hanke. |
| 4,412,833 | 11/1983 | Wiegner et al. ............ 604/14 |
| 4,508,531 | 4/1985 | Whitehead ................. 604/14 |
| 4,900,299 | 2/1990 | Webb. |
| 5,002,526 | 3/1991 | Herring. |
| 5,317,052 | 5/1994 | Ohba et al.. |
| 5,346,468 | 9/1994 | Campion et al. .......... 604/13 |
| 5,395,308 | 3/1995 | Fox et al. .................. 604/14 |

Primary Examiner—John G. Weiss
Assistant Examiner—Dennis Ruhl
Attorney, Agent, or Firm—Ohlandt, Greeley, Ruggiero & Perle

[57] ABSTRACT

A tampon applicator having a barrel and a plunger telescopically mounted within the barrel. In a preferred embodiment, one or both of the barrel and plunger is made of a water dispersible material, preferably polyvinyl alcohol resin, and is exposed to infrared radiation to minimize surface stickiness on initial contact with moisture. In an alternative embodiment, the barrel or plunger can be coated with a polyvinyl alcohol coating prior to exposure to infrared radiation.

26 Claims, 1 Drawing Sheet

INFRARED TREATED TAMPON APPLICATORS

The present invention is directed to an improved tampon applicator. More particularly, the present invention is directed to a tampon applicator having a plastic-type body or coating that has been treated. Even more particularly, the tampon applicator is molded of polyvinyl alcohol resin with the outside surface of the applicator treated with infrared radiation.

BACKGROUND OF THE INVENTION

Tampon applicators are desired by consumers. Since a polyvinyl alcohol (also referred to herein as "PVOH") applicator is water soluble, it has been previously suggested for making flushable tampon applicators. However, PVOH is known to become sticky on contact with moist surfaces or under humid conditions. Heat treatment to the PVOH applicator leads to crystallization that increases water resistance, but too much heat makes PVOH unacceptably stiff. The present invention overcomes this disadvantage by heating only the outside of the applicator with infrared radiation.

The assignee of the present invention has a co-pending application, Ser. No. 08/632,201, filed on Apr. 15, 1996, that discloses a novel set of plasticizers suitable for use with PVOH that, in conjunction, produce a molded product having improved stability, ease of molding, and utility for tampon applicators. The disclosure of that application is herein incorporated by reference.

Tampon applicators typically are constructed from two telescoping tubes. One tube, a barrel, encloses the pledget, and the other tube, a plunger, is used to eject the pledget out of the barrel during insertion. Thus, it is essential that the tubes telescope smoothly to facilitate ejection. Any stickiness or other adhesions between the two tubes can make insertion difficult, painful, or impossible. If the plunger is much less in diameter than the barrel to prevent sticking together, the plunger will most likely disassemble from the barrel.

Furthermore, the ability of the barrel to be inserted smoothly, without dragging on the delicate vaginal tissue, is very important not only for users comfort but also for proper insertion of the pledget. Once again, any stickiness or adhesion sites on the outer surface of the barrel will impede proper insertion.

Tampon applicators formed from PVOH resin, when dry, have glide characteristics similar to traditional plastic tampon applicators. Thus, PVOH tampon applicators would be expected to have optimal qualities for insertion, minimal drag on insertion and smooth telescoping of the barrel and plunger. Yet, PVOH tampon applicators remain dispersible and biodegradable on disposal in water.

However, the very ability of the PVOH tampon applicators to disperse in water also creates certain drawbacks. PVOH can become sticky on contact with moist surfaces, bodily fluids or under humid conditions. Thus the PVOH tampon applicator tends to become tacky in the very environment for which it is designed. This in turn makes insertion more difficult, since the outer tube can become gummy or tacky upon insertion. Another potential problem should the PVOH applicator be exposed to moisture, is that the barrel and plunger may not telescope properly. The barrel and plunger may even become glued together, requiring a much greater force to eject the tampon pledget from the applicator. Additionally, humidity from the environment can permeate the packaging used to store the PVOH tampon applicator and, thus, cause the same problems. Humidity may even cause the applicator to stick to the wrapper.

SUMMARY OF THE INVENTION

Accordingly, it is an object of the present invention to provide a water dispersible tampon applicator that has been treated with infrared radiation to avoid or minimize adverse moisture effects on the tampon applicator.

It is another object of the present invention to provide a polymer tampon applicator that has been treated with infrared radiation so that the applicator will not become sticky or begin to biodegrade upon initial contact with moist surfaces, bodily fluids or ambient humidity.

It is a further object of the present invention to provide a cardboard tampon applicator that has been coated with a water dissolvable coating and then treated with infrared radiation so that the applicator will not become sticky or begin to biodegrade upon initial contact with moist surfaces, bodily fluids or ambient humidity.

It is still a further object of the present invention to provide a PVOH tampon applicator that has been treated with infrared radiation so that the outside surface is crystallized to increase water resistance, yet the applicator remains flexible and, thus, usable.

Accordingly, the present invention discloses a tampon applicator having a barrel and a plunger that is telescopically mounted within the barrel. Either or both the barrel or plunger is made of a water dispersible plastic, preferably a polyvinyl alcohol resin, or cardboard treated with a water-dispersible plastic coating. The barrel or plunger is exposed to or treated with infrared radiation to minimize surface stickiness thereof when exposed to moisture.

DESCRIPTION OF THE PREFERRED EMBODIMENTS

Figure 1:
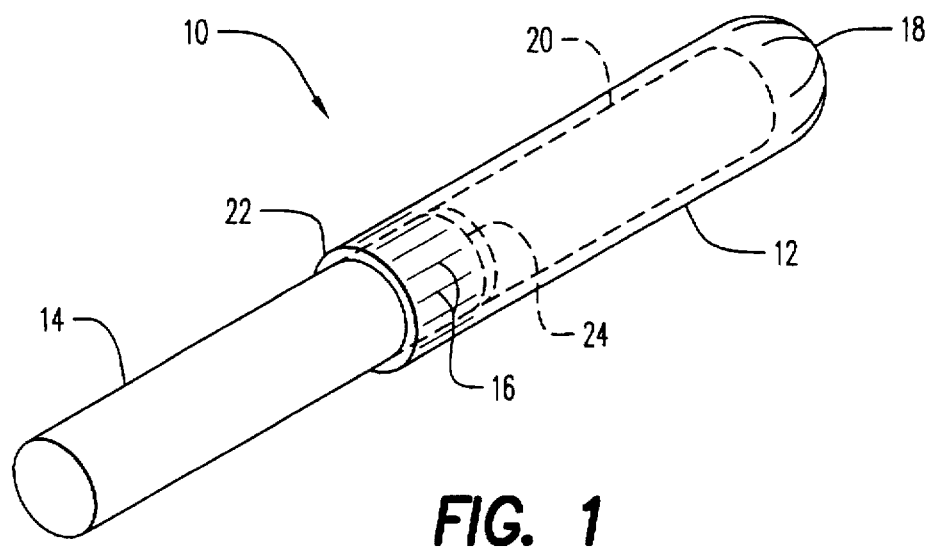
FIG. 1 is a perspective view of a tampon applicator employing a preferred method of the present invention.

Referring to the drawings and, in particular, FIG. 1, there is a tampon applicator generally represented by reference numeral 10. The applicator 10 has an outer tube or barrel 12 and an inner tube or plunger 14. The barrel 12 preferably has a curved or petal tipped end 18, and a plunger insertion end 22. The barrel 12 preferably has a plurality of fingergrips 16. The plunger 14 has an insertion end which has an edge 24. Upon assembly, pledget 20 is located within barrel 12, and plunger 14 is inserted in end 22 of barrel 12. The edge 24 of plunger 14 will act against pledget 20 when the plunger 14 is moved to eject pledget 20 through and out of end 18 of barrel 12.

The barrel 12 and plunger 14 can be made of any water dispersible material, such as, for example, polyvinyl alcohol (PVOH), cardboard and starch based materials. However, it is preferable that either or both be made of PVOH.

Alternatively, either or both the barrel 12 and plunger 14 may be made of other materials, and then coated with a water dispersible coating, such as, for example, PVOH, prior to the infrared treatment of the present invention.

In one preferred embodiment, barrel 12 and plunger 14 are made of PVOH. In a second preferred embodiment, the barrel is made of PVOH, and the plunger is made of another material, such as cardboard.

Figure 2:
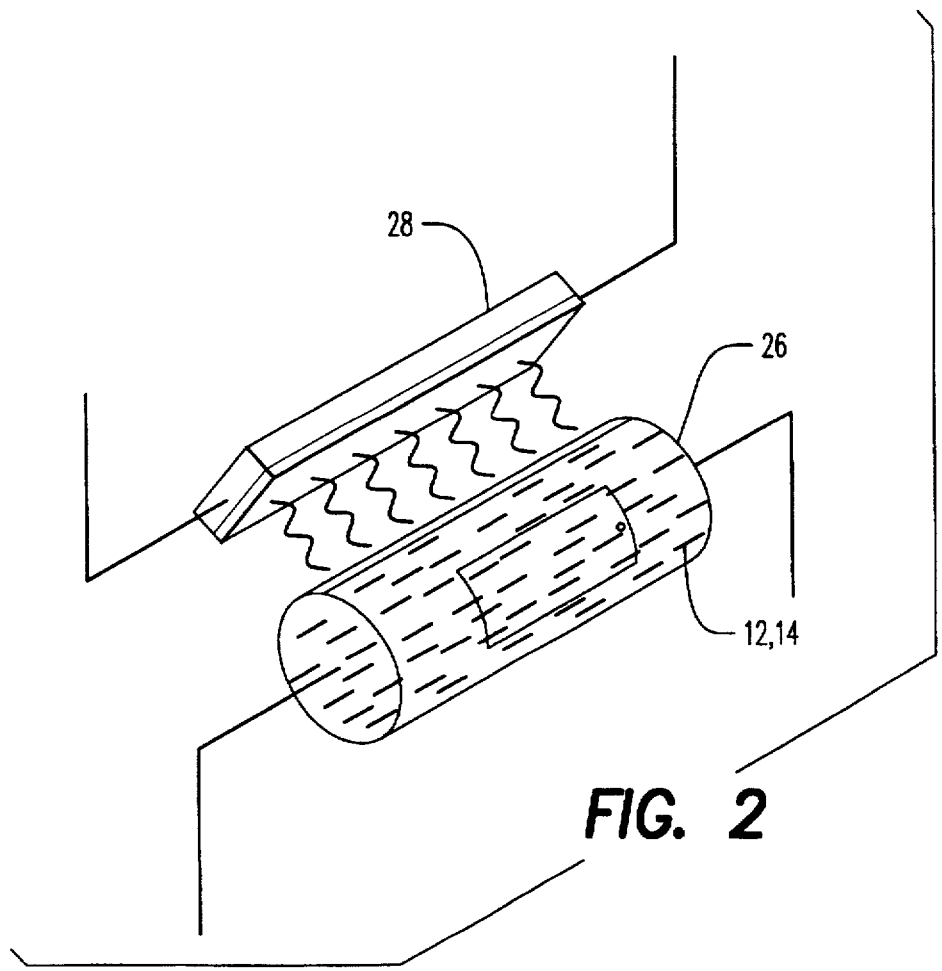
FIG. 2 is a diagram of a preferred method of treating a tampon applicator according to the present invention.

The tampon applicator assembly includes the barrel 12 and plunger 14 assembled together with the pledget 20 in the barrel. As shown in FIGS. 2, the tampon applicator assembly is placed in a rotating carrier 26. The barrel 12 and plunger 14 are rotated in the rotating carrier 26 while the carrier is subjected to infrared (or "IR") radiant heater or heaters 28. As shown in FIG. 2, the heater 28 is positioned approximately 6 inches from the carrier 26. The barrel 12 and plunger 14 are preferably treated with the infrared radiant heater 28 from about five to about sixty seconds at temperatures from about 700° F. to about 2500° F. The most preferred conditions for infrared treatment are:

|  | Time (seconds) | Temperature (°F.) |
|---|---|---|
| Condition A | 40 | 1325 |
| Condition B | 20 | 1750 |

The infrared treatment affects the outer surface of the tampon applicator 10 by inducing high temperature molecular crystallinity along the backbone of the PVOH. This results in a more hydrophobic surface thereby providing a less sticky surface.

This infrared treatment does not destroy, deform or degrade the petals of the applicator. Thus, this entire tampon applicator can be treated, whereas other known treatments would affect the petals. In prior treatments, the petals required protection during treatment, i.e. only the applicator body minus the petals could be treated.

The PVOH tampon applicators treated with infrared treatment demonstrate substantially improved performance in comparison with the conventional, not IR treated PVOH applicators. A home use test of 100 respondents was performed. Specifically, tampons having (1) PVOH barrels infrared treated as set forth above (with untreated cardboard plungers); and (2) untreated applicators having barrels and plungers of traditional polyethylene were tested.

| Attribute | # Preferring IR Treated PVOH | # Preferring Untreated Polyethylene | No Preference | Preference Ratio |
|---|---|---|---|---|
| Easy to insert | 32 | 29 | 39 | +1.1 |
| Comfortable to Insert | 29 | 25 | 46 | +1.1 |
| Easy to Eject From Applicator | 32 | 29 | 45 | +1.1 |
| Easy to Grip | 25 | 22 | 53 | +1.1 |
| Overall Comfort | 28 | 20 | 52 | +1.2 |
| Smoothness of Applicator | 27 | 23 | 35 | +1.1 |
| The applicator | 38 | 38 | 24 | 1.0 |

A similar study was conducted comparing untreated PVOH applicators to traditional, untreated polyethylene applicators. All applicators were the same in size, shape, dimensions and fingergrip. The results below show that consumers clearly preferred the untreated polyethylene applicators to untreated PVOH applicators.

| Attribute | # Preferring Untreated PVOH | # Preferring Untreated Polyethylene | No Preference | Preference Ratio |
|---|---|---|---|---|
| Easy to insert | 13 | 43 | 28 | -2.1 |
| Comfortable to Insert | 14 | 42 | 28 | -2.0 |
| Easy to Eject From Applicator | 11 | 38 | 35 | -1.9 |
| Easy to Grip | 20 | 15 | 49 | +1.1 |
| Overall Comfort | 8 | 22 | 54 | -1.4 |
| Smoothness of Applicator | 8 | 43 | 33 | -2.4 |
| The applicator | 26 | 40 | 18 | -1.4 |

In summary, the results of these two tests show consumers clearly prefer the infrared treated PVOH (as compared to untreated polyethylene applicators) over untreated PVOH applicators. When comparing the preference ratios derived from the first experiment with infrared treated PVOH applicators (center column, below) versus untreated PVOH applicators the difference is obvious. This demonstrates the dramatic difference in product acceptability that is conferred by the infrared treatment of the present invention.

|  | Preference Ratio IR Treated PVOH | Preference Ratio Untreated PVOH |
|---|---|---|
| Comfortable to insert | +1.1 | -2.0 |
| Easy to insert | +1.1 | -2.1 |
| Easy to eject | +1.1 | -1.9 |
| Easy to grip | +1.1 | +1.1 |
| Smoothness of applicator | +1.1 | -2.4 |
| The applicator | +1.0 | -1.4 |
| Overall comfort | +1.2 | -1.4 |

Accordingly, the IR treated PVOH applicator has similar consumer acceptance ratings to the traditional polyethylene applicator, even before taking into account the consumer preference for flushable and biodegradable applicators. This is a substantial improvement over the results for the untreated PVOH applicator. Furthermore, the IR treated PVOH may have scored even better with a treated PVOH plunger instead of the cardboard plunger used in the test.

Thus, it will be obvious to one of ordinary skill in the art that the foregoing description and drawings are merely illustrative of certain preferred embodiments of the present invention, and that various obvious modifications can be made to these embodiments in accordance with the spirit and scope of the appended claims.

What is claimed is:

1. A tampon applicator comprising:
    a barrel having an outer surface and a first end, said barrel being made of polyvinyl alcohol; and
    a plunger adapted to be telescopically mounted in the first end of said barrel,
    wherein said outer surface of said barrel is treated by infrared radiation to minimize surface stickiness on initial contact with moisture.

2. The tampon applicator of claim 1, wherein said plunger is made of a material selected from the group consisting of polyvinyl alcohol and cardboard.

3. The tampon applicator of claim 1, wherein said plunger is made of polyvinyl alcohol.

4. The tampon applicator of claim 1, wherein said plunger is coated with polyvinyl alcohol.

5. The tampon applicator of claim 4, wherein said said plunger is coated with polyvinyl alcohol.

6. The tampon applicator of claim 1, wherein said infrared radiation is generated by a radiant heater.

7. The tampon applicator of claim 1, wherein said infrared radiation comprises exposing said barrel to infrared radiation from about 5 to about 60 seconds at about 700° F. to about 2500° F.

8. A tampon applicator comprising:
   a barrel having an outer surface and a first end; and
   a plunger adapted to be telescopically mounted in the first end of said barrel,
   wherein said outer surface of said barrel is coated with a coating containing polyvinyl alcohol and said coated barrel is then treated by infrared radiation to minimize surface stickiness on initial contact with moisture.

9. The tampon applicator of claim 8, wherein said plunger is made of a material selected from the group consisting of polyvinyl alcohol and cardboard.

10. The tampon applicator of claim 8, wherein said plunger is coated with polyvinyl alcohol.

11. The tampon applicator of claim 8, wherein said infrared radiation is generated by a radiant heater.

12. The tampon applicator of claim 8, wherein said infrared radiation comprises exposing said barrel to infrared radiation from about 5 to about 60 seconds at about 700° F. to about 2500° F.

13. A tampon applicator comprising:
   a barrel having an outer surface and a first end, said barrel being made of cardboard, said outer surface being coated with polyvinyl alcohol; and
   a plunger telescopically mounted in the first end of said barrel,
   wherein said barrel is exposed to infrared radiation, prior to said tampon applicator being used, to minimize surface stickiness of said tampon applicator on initial contact with moisture.

14. A tampon applicator comprising:
   a barrel having a first outer surface and a first end, said barrel being made of polyvinyl alcohol; and
   a plunger telescopically mounted in the first end of said barrel, said plunger having a second outer surface, said second outer surface being coated with polyvinyl alcohol,
   wherein said first and second outer surfaces are exposed to infrared radiation, to minimize stickiness of said tampon applicator on initial contact with moisture.

15. The tampon applicator of claim 14, wherein said plunger is made of cardboard.

16. A method for treating a tampon applicator having a barrel coated with polyvinyl alcohol and having a plunger, said method comprising:
   subjecting said coated barrel to a source of infrared radiation.

17. The method of claim 16, wherein said barrel is subjected to said source of infrared radiation from about 5 to about 60 seconds.

18. The method of claim 16, wherein said source of infrared radiation subjects said barrel to a temperature from about 700° F. to about 2500° F.

19. The tampon applicator of claim 16, wherein said plunger is made of cardboard.

20. The tampon applicator of claim 16, wherein said plunger is made of, or coated with, polyvinyl alcohol.

21. A method for treating a tampon applicator having a barrel made of polyvinyl alcohol and having a plunger, comprising:
   subjecting said coated barrel to a source of infrared radiation.

22. The method of claim 21, wherein said barrel is subjected to said source of infrared radiation from about 5 to about 60 seconds.

23. The method of claim 21, wherein said source of infrared radiation subjects said barrel to a temperature from about 700° F. to about 2500° F.

24. The method of claim 21, wherein said plunger is made of cardboard.

25. The method of claim 21, wherein said plunger is made of a polymer.

26. The method of claim 21, wherein said plunger is made of polyvinyl alcohol.

* * * * *